United States Patent [19]

Hecking

[11] Patent Number: 4,712,737
[45] Date of Patent: Dec. 15, 1987

[54] AIR FRESHENER CONTAINER HAVING RESEALABLE OPENINGS

[75] Inventor: Robert J. Hecking, Passaic, N.J.

[73] Assignee: Champion International Corporation, Stamford, Conn.

[21] Appl. No.: 764,017

[22] Filed: Aug. 9, 1985

[51] Int. Cl.$^4$ .................................................. A61L 9/04
[52] U.S. Cl. ........................................ 239/58; 206/0.5; 229/75; 229/35 MF
[58] Field of Search .................................. 239/57-60, 239/34.6, 58, 59; 206/620, 625, 626; 229/8, 170 C, 75, 3.1, 3.5 MF, 17 G, 631, 633; 383/66

[56] References Cited

U.S. PATENT DOCUMENTS

| | | | |
|---|---|---|---|
| 1,806,149 | 5/1931 | Daugherty | 239/57 |
| 2,111,025 | 3/1938 | Galler | 239/57 |
| 2,352,075 | 6/1944 | Brownstein | 239/58 |
| 2,661,138 | 12/1953 | Leonard | 229/17 G |
| 2,896,839 | 7/1959 | Barnes et al. | 206/626 |
| 3,184,149 | 5/1965 | Repko | 383/66 X |
| 3,233,795 | 2/1966 | Struble | 229/1.7 R X |
| 3,239,126 | 3/1966 | Arslanian | 229/35 MF |
| 3,317,107 | 5/1967 | Williams | 229/3.5 MF |
| 3,471,871 | 10/1969 | Nociti et al. | 383/66 X |
| 3,711,011 | 1/1973 | Kugler | 206/626 X |
| 3,770,185 | 11/1973 | Reeves | 229/17 G |
| 3,946,945 | 3/1976 | Odioso et al. | 239/58 |
| 4,219,145 | 8/1980 | Jaeschke et al. | 239/60 |
| 4,244,474 | 1/1981 | Wise | 229/17 G |
| 4,445,641 | 5/1984 | Baker et al. | 239/6 |

Primary Examiner—Duane A. Reger
Assistant Examiner—Kevin Patrick Weldon
Attorney, Agent, or Firm—Evelyn M. Sommer

[57] ABSTRACT

A container for an air freshener having a gabled top. Openings sealed with removable tape are provided in the carton to expose the contents to the air. The openings may also comprise reverse cut slots which expose the interior when the consumer presses on the slots. The gable top container is formed from a single ply of foil laminated lined paperboard. In the preferred embodiment a plurality of openings are formed in the paperboard and are covered by a release tape which can be removed to permit exposure of less than all of the openings depending on the amount of air freshener to be exposed to the atmosphere.

7 Claims, 9 Drawing Figures

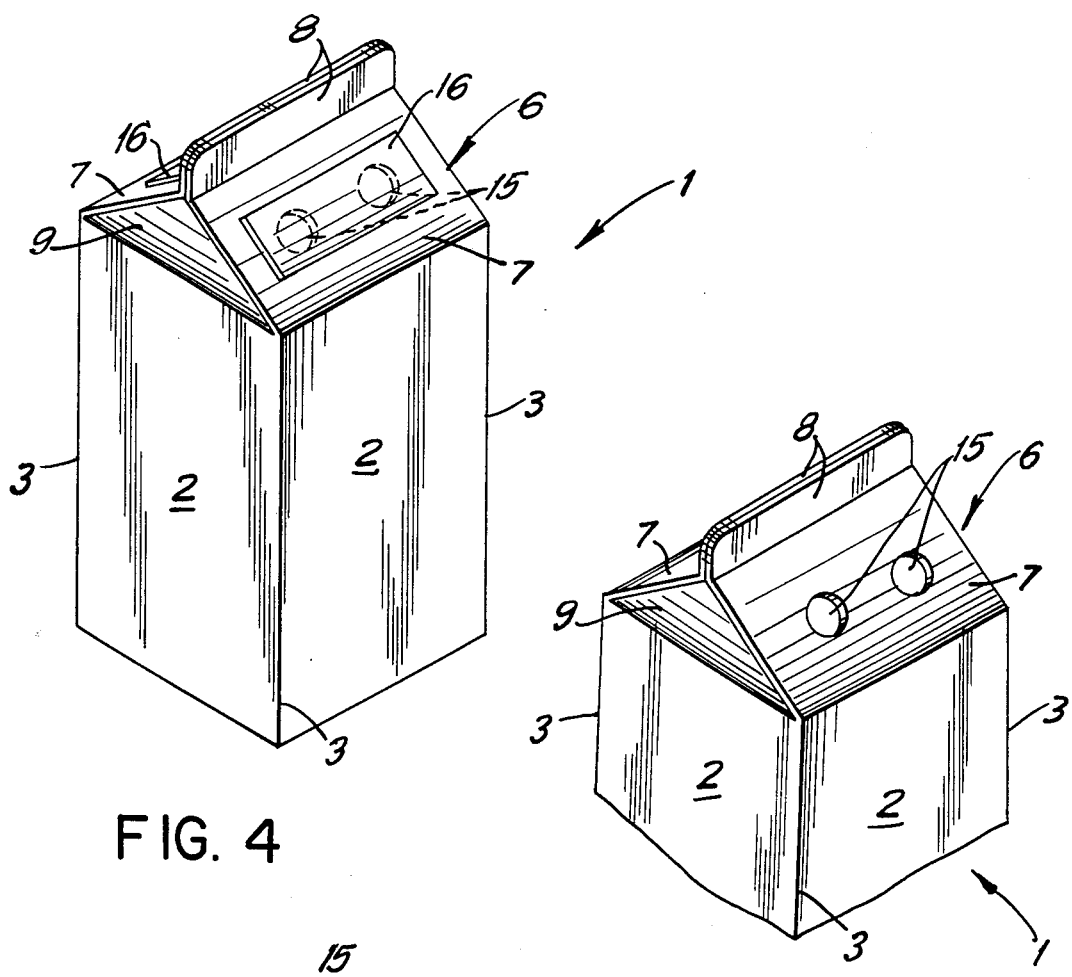

AIR FRESHENER CONTAINER HAVING RESEALABLE OPENINGS

BACKGROUND OF THE INVENTION

The present invention is directed to an improved container for air freshening and, more particularly, a more cost effective container than current air fresheners.

In the past air fresheners have been packaged in many types of containers. Many of these containers have been made of paperboard, plastic or other suitable materials. Such containers have assumed many shapes and have been adapted to be hung, or to stand on shelves, or to adhere to walls, furniture and windows. For purposes of definition, an air freshener consists of three elements: (1) the air freshening fragrance, (2) a fragrance delivery media (a material to hold the fragrance in the container and when exposed to air help diffuse it, and (3) the container.

When closed the container must not allow the highly diffusive air freshening fragrance to escape or permeate through its walls. Many plastics and other materials allow high percentages of fragrance to escape from the container by passing (permeating) through the plastic itself at the score of fold lines, or between halves near closure points. Thus the air freshener loses efficacy even before purchase or use. After opening, the container must not allow air flow to enter the container and fragrance to escape as completely as possible to insure maximum effectiveness. The container must also be aesthetically pleasing so it can be placed closest to the desired zone of freshening (near consumer).

To date the most commercially successful air fresheners employ relatively thick (to prevent permeating), expensive custom molded plastic containers with costly machined orifices. Due to the price sensitivity in the air freshener market and the high cost of this packaging, marketers have been forced to reduce the amount of air freshening fragrance and the cost/quality of the fragrances. This has reduced the efficacy and perhaps accounts for lost sales volume (declining consumer confidence in their efficacy).

SUMMARY OF THE INVENTION

The present invention overcomes these objections and is directed at an improved, cost effective container which allows marketers to increase air freshening fragrance quantity and quality, thus improving efficacy.

In accordance with the invention, there is employed for containment of the air freshener a container similar to a standard milk carton and preferably one having a gabled top. Means, such as openings sealed with removable tape, are provided in the carton to expose the contents to the air. The openings also preferably comprise reverse cut slots which expose the interior when the consumer presses on the slots.

BRIEF DESCRIPTION OF DRAWINGS

A preferred embodiment of the invention has been chosen for purposes of illustration and description and is shown in the accompanying drawings forming a part of the specifications.

FIG. 4 is a perspective view showing another embodiment of the present invention.

FIG. 5 is a fragmentary perspective view showing the container ready to be used.

FIG. 6 is a top view of the container.

Figure 1:
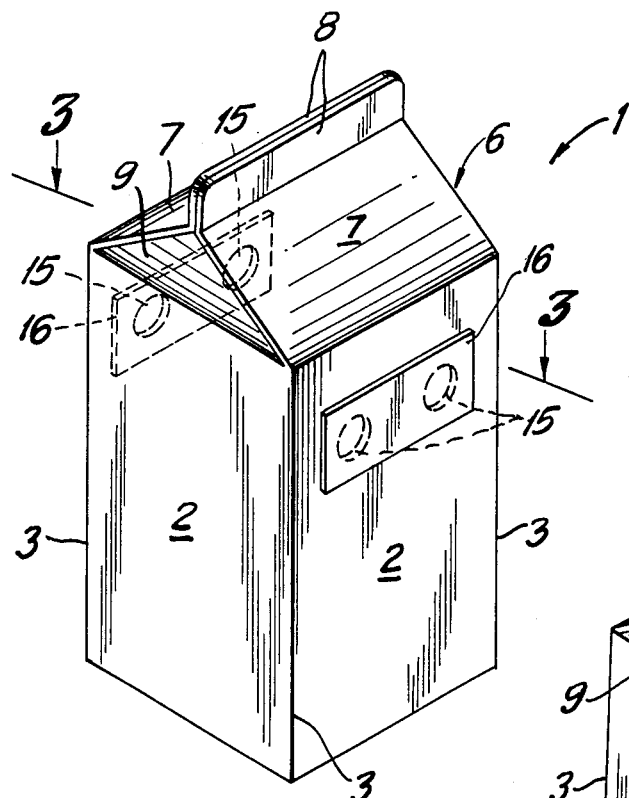
FIG. 1 is a perspective view showing one embodiment of the container made in accordance with the present invention.

Using greatly increased fragrance levels, 6% 150 grams fill or 9 grams of fragrance, the container performed as follows:

(1) Fragrance Containment
  a. When closed or sealed foil lined paperboard containers hold the air freshening fragrance in the container allowing only 1.9% (max) to escape in eight weeks at room temperature.
  b. When closed or sealed the foil lined paperboard containers hold the air freshening fragrance in the container allowing only 4% maximum to escape in eight weeks at 130° F.
  c. In unlined paperboard containers losses were much higher, up to 18%.
  d. Heat shrink wrapping on closed sealed foil lined containers cut losses in the sealed container to 0.95% at room temperature, and 5.5% at 130° F.

(2) Fragrance Diffusion

Using various orifice designs as for instance shown in the drawings, several fragrance delivery media (blotter, diatomaceous earth, wax, carrageenan gel, pressed plastic powders, polymers containing fragrance) were evaluated for fragrance loss. 150 grams carrageenan gel containing 6% fragrance level or 9 grams of air freshening fragrance lost 85-88% of weight in eight weeks and 70-72% of weight in four weeks. By varying orifice size in FIG. 7, 8, 9 to ¼"×1" from ⅜"×2" weight loss could be controlled to a satisfactory level for an eight week period. Thus the invention container with gel is an excellent diffuser of air freshening fragrance.

(3) Package Aesthetics The container can be directly printed with many attractive designs making them suitable for display in the home, office, hospital room, etc., hence increasing their sales and acceptance by the consumer.

(4) Cost Effectiveness The cost effectiveness of the paperboard container as compared to plastic, glass and metal containers heretofore used will allow marketers to utilize more air freshening fragrance and increase effectiveness of the product.

DESCRIPTION OF THE INVENTION

Figure 2:
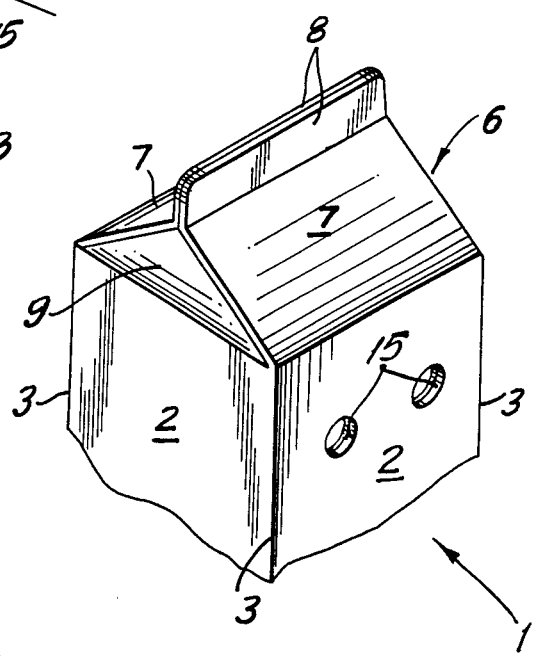
FIG. 2 is a fragmentary perspective view showing the container ready for use.
Figure 3:
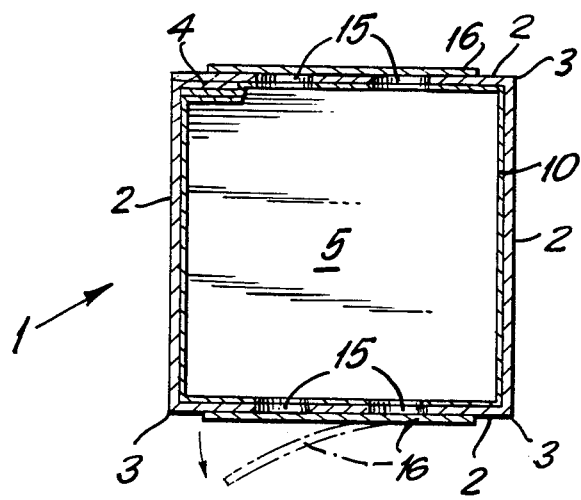
FIG. 3 is a sectional view taken along line 3—3 of FIG. 1.

Referring to the drawings and particularly the embodiment shown in FIGS. 1 to 3, the container 1 of the present invention comprises a plurality of side walls 2 which are folded relative to each other along fold lines 3 and which are assembled together by means of a glue flap 4 (FIG. 3) to form a rectangular configuration. The container 1 is provided with a bottom wall 5 and a gabled top assembly 6 comprising a pair of inclined top walls 7 adhered together along substantially vertical top flaps 8 and forming inclined end walls 9. The inner surfaces of the walls 2, 5 and 7 may be lined with aluminum foil liner 10 as shown in FIG. 3. The basic construction of other containers of the type, as exemplified in U.S. Pat. Nos. 3,308,996; 4,224,092; and 4,126,262. The container 1 is packaged with an air freshener which may consist of any well known air freshener product. Preferably, the fragrance delivery media is a carrageenan gel system using an emulsifier blend to increase fragrance solubility above normal. As instances of other suitable materials for holding the fragrance in the container and when exposed to the air helping to diffuse it, i.e., fragrance delivery media, there may be utilized in accordance with the invention, woven and unwoven adsorbent fiber materials, diatomaceous earths, clays, synthetic films, fibers and gels, ceramic bodies, paradichloro benzene, fragrance solutions and emulsions.

The emulsifier blend is used at a ratio of 1 to 1 with perfume oil. The emulsifier blend consists of three parts Span 60 to two parts Tween 60. The fragrance level is preferably 6% and the container of the present invention is preferably adapted to contain 150 grams of this air freshener product.

In the embodiment shown in FIGS. 1 to 3, a plurality of openings 15 are formed in the side walls of the container 1. These openings 15 are shown in the drawings as being circular but, of course, may assume any desired shape without departing from the invention. The openings 15 here shown as circular can be of any number or shape and are adapted to be covered by a release tape 16 so that the contents are not exposed to the air until the container is ready to be used. When the container is to be used, the tapes 16 are removed to expose the openings 15 and to permit the air freshener to escape into the atmosphere. It will be noted that in this embodiment a pair of openings 15 are formed adjacent to each other with each pair covered by a single tape 16. This permits the user to expose some of the openings and leave other openings covered depending upon the amount of air freshener the user desires to to expose to the air. Preferably, the openings are in the upper portion of the container. However, it will of course be understood that the number, shape and location of the openings 15 may vary and that the openings 15 may be individually closed by separate tapes 16, if desired.

The embodiment shown in FIGS. 4 to 6 is similar to the embodiment shown in FIGS. 1 to 3. However, in this embodiment, the openings 15 and the releasable tapes 16 are located in the inclined top walls 7. Again, the contents of the container 1 are exposed to the atmosphere by removing one or more of the covering tapes 16.

Figure 7:
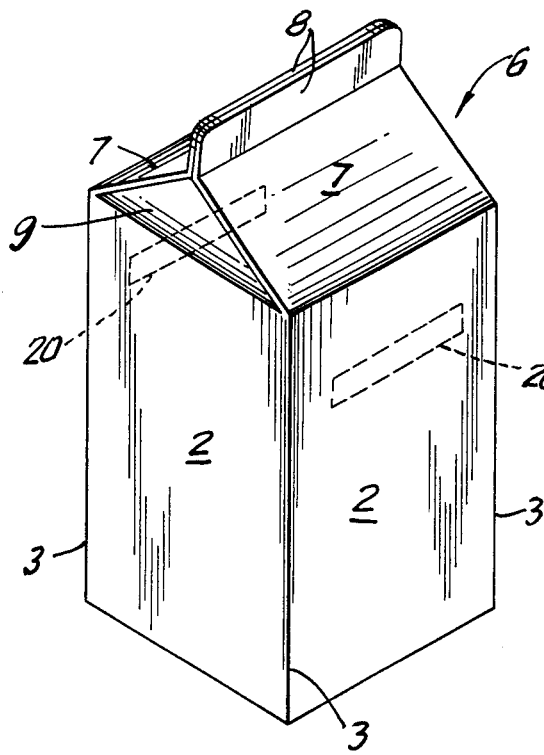
FIG. 7 is a perspective view of still another embodiment of the present invention.
Figure 8:
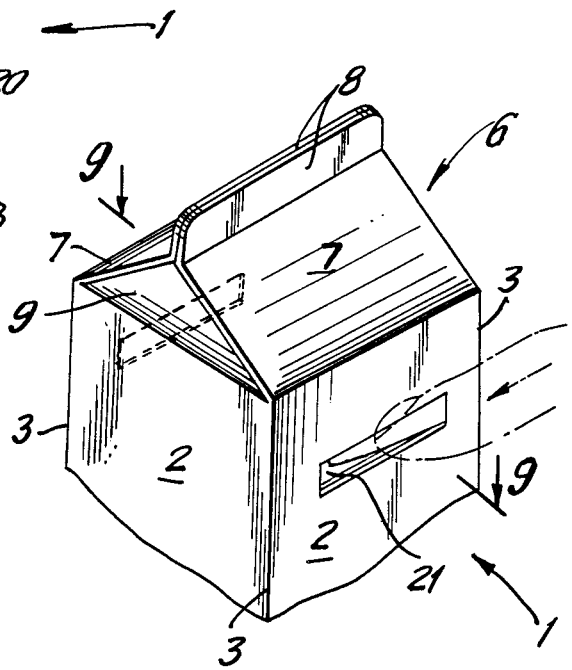
FIG. 8 is a fragmentary sectional view showing the manner of activating the container.
Figure 9:
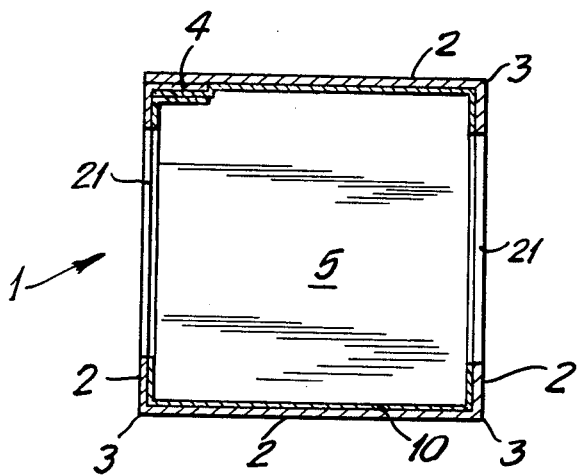
FIG. 9 is a sectional view taken along line 9—9 of FIG. 8.

The embodiment shown in FIGS. 7 to 8, which is the preferred embodiment of the invention, has substantially the same construction as the embodiments shown in FIGS. 1 to 3 and FIGS. 4 to 6. However, in this embodiment, the use of tapes 16 to cover pre-formed openings is avoided. The side walls 2 of the container are provided with reverse cut perforations 20 to form slots 21 thereby exposing the contents of the container 1 to the atmosphere. It will be understood that the number of openings 21 as well as the shapes and locations of the openings 21 may vary without departing from the invention. In addition, if desired, the user may control the amount of air freshener which is exposed to the air by opening certain openings 21 and keeping others closed.

It will thus be seen that the present invention provides an improved container for an air freshener which may be opened without the use of any mechanical devices as for example close tolerance screw tops, sliding tracks which by their very nature are expensive and difficult to manufacture.

As many and varied modifications of the subject of this invention will become apparent to those skilled in the art from the detailed description given herein above, it will be understood that the present invention is limited only as provided in the claims appended hereto.

The embodiments of the invention in which an exclusive property or privilege is granted are defined as follows:

1. An air freshener package comprising a unitary folded container formed of a single ply of foil laminated lined paperboard having two opposed pairs of upstanding side walls, a bottom wall and a gable top comprising a pair of inclined top walls and a pair of top flaps articulated to the respective top walls and adhered in face-to-face relationship to securely seal the container top; and an air freshener contained therein, a plurality of openings formed in said single ply of foil laminated lined paperboard in said gable top of said container, said openings being covered by a release tape which can be removed permitting exposure of less than all of the openings depending on the amount of air freshener desired to be exposed to the atmosphere.

2. A package as claimed in claim 1 wherein the air fresher comprises a fragrance delivery media which includes a carrageenan gel system using an emulsifier blend to increase fragrance solubility above normal, said emulsifier blend being at a ratio of 1 to 1 with a perfume oil and consisting of three parts Span 60 to two parts Tween 60 with the fragrance level being 6%.

3. A package as claimed in claim 2 utilizing as fragrance delivery media a member selected from the group consisting of woven and unwoven absorbent fiber materials, diatomaceous earths, clays synthetic films, fibers and gels, ceramic bodies, paradichlorobenzene, fragrance solutions and emulsions.

4. An air freshener package comprising a unitary folded container formed of a single ply of foil laminated lined paperboard having two opposed pairs of upstanding side walls, a bottom wall and a gable top comprising a pair of inclined top walls and an air freshener contained therein, at least one of said side walls being provided with a plurality of openings formed in said single ply of foil laminated lined paperboard, said openings being covered by a release tape which can be removed permitting exposure of less than all of the openings depending on the amount of air freshener to be exposed to the atmosphere.

5. A package as in claim 4, wherein said openings are located in the upper portion of at least one of said side walls.

6. A package as claimed in claim 4 wherein the air freshener comprises a fragrance delivery media which includes a carrageenan gel system using a emulsifier blend to increase fragrance solubility above normal, said emulsifier blend using at ratio of 1 to 1 with a perfume oil and consisting of three parts Span 60 to two parts Tween 60 with the fragrance level being 6%.

7. A package as claimed in claim 6 utilizing a fragrance delivery media a member selected from the group consisting of woven and unwoven absorbent fiber material, diatomaceous earths, clays, synthetic films, fibers and gels, ceramic bodies, paradichlorobenzene, fragrance solutions and emulsions.

* * * * *

UNITED STATES PATENT AND TRADEMARK OFFICE
CERTIFICATE OF CORRECTION

PATENT NO.  : 4,712,737
DATED       : December 15, 1987
INVENTOR(S) : Robert J. Hecking It is certified that error appears in the above—identified patent and that said Letters Patent is hereby corrected as shown below:

Title page:

In addition to Champion International Corporation please add assignee "Robertet, Inc., Oakland, New Jersey Signed and Sealed this Thirteenth Day of December, 1988

Attest:

DONALD J. QUIGG

*Attesting Officer*         *Commissioner of Patents and Trademarks*